United States Patent [19]

Abramowicz et al.

[11] Patent Number: 4,892,822
[45] Date of Patent: Jan. 9, 1990

[54] ENZYME-CATALYZED REACTIONS INVOLVING DIPHENYL CARBONATE

[75] Inventors: Daniel A. Abramowicz, Ballston Spa; Charles R. Keese, Schoharie, both of N.Y.

[73] Assignee: General Electric Company, Schenectady, N.Y.

[21] Appl. No.: 111,248

[22] Filed: Oct. 22, 1987

[51] Int. Cl.[4] .......................... C12P 7/00; C08G 63/62
[52] U.S. Cl. ..................................... 435/132; 528/196
[58] Field of Search ......................... 435/132; 528/196

[56] References Cited

PUBLICATIONS

Biotechnology and Bioengineering, J. Dorkick et al., "Polymerization of Phenols Catalyzed by Perosidase in Nonaqueous Media", vol. XXX, (1987), pp. 31–36.

Biochemistry, Y. Pocker et al., "Carbonic Anhydrase Catalyzed Hydrolysis and Decarboxylation, Kinetic Studies of Enzyme-Catalyzed Decomposition of Mono- -and Disubstituted Derivatives of Carbonic Acid", vol. 13, No. 1, 1974, pp. 70–78.

American Chemical Society, W. E. Ladner et al., "Lipase-Catalyzed Hydrolysis as a Route to Esters of Chiral Epoxy Alcohols", (1984), pp. 7250–7251.

American Chemical Society, G. Kirchner et al., "Resolution of Racemic Mixtures via Lipase Catalysis in Organic Solvents", (1985), pp. 7072–7076.

Biotechnology and Bioengineering, R. Kazandjian et al., "Enzymatic Analyses in Organic Solvents", vol. XXVIII, (1986), pp. 417–421.

"Peptide and Ester Synthesis in Organic Solvents Catalyzed by Seryl Proteases Linked to Alumina", M. Pugniere et al., Proteins, Alan R. Liss, Inc. (1986), pp. 134–138.

Biotechnology and Bioengineering, R. G. Ingalls et al., "Reversal of Enzymatic Hydrolysis: Rate and Extent of Ester Synthesis as Catalyzed by Chymotrypsin and Subtilisin Carlsberg at Low Water Concentrations", (1975), pp. 1627–1637.

Annals New York Academy of Sciences, I. L. Gatfield, "The Enzymatic Synthesis of Esters in Nonaqueous Systems", pp. 569–572.

Biochemistry, Y. Pocker et al., "Catalytic Versatility of Erythrocyte Carbonic Anhydrase. Kinetic Studies of the Enzyme–Catalyzed Hydrolysis of Methyl Pyridyl Carbonates", vol. 11, No. 2 (1972), pp. 180–190.

Biochemical and Biophysical Research Communications, Y. Inada et al., "Ester Synthesis Catalyzed by Polyphenylene Glycol–Modified Lipase in Benzene", vol. 122, No. 2 (1984), pp. 845–850.

Proteins: Structure, Function, and Genetics, "Proteins and Peptides in Water-Restricted Environments", M. Waks, pp. 4–15, (including Comment on Dry Enzymes by Cyrus Levinthal, 1986, Alan R. Liss, Inc.

*Primary Examiner*—Ronald W. Griffin
*Assistant Examiner*—Pamela S. Webber
*Attorney, Agent, or Firm*—William H. Pittman; James C. Davis, Jr.

[57] ABSTRACT

Enzyme-catalyzed exchange reactions with diphenyl carbonate compounds are disclosed. Nucleophiles participating in these reactions include water and a wide range of hydroxy-containing compounds. Polycarbonate products can be prepared according to this invention by the use of various bisphenols in a transesterification reaction with the diphenyl carbonate compound.

19 Claims, 2 Drawing Sheets

ENZYME-CATALYZED REACTIONS INVOLVING DIPHENYL CARBONATE

This invention relates to hydrolysis and transesterification reactions involving diphenyl carbonate.

The use of enzymes as catalysts in organic synthesis is a well-recognized technique. Reference is made, for example, to *Polymerization of Phenols Catalyzed By Peroxidase In Nonaqueous Media*, J. Dordick et al., *Biotechnology and Bioengineering*, Volume XXX, pages 31-36 (1987), wherein polymers are produced by horseradish-peroxidase-catalyzed coupling of phenols. In addition to enzyme-catalyzed polymerization reactions, other organic reactions have also been studied. For example, Y. Pocker et al. discuss the enzyme-catalyzed hydrolysis of a carbonate diester in *Biochemistry*, Volume 13, No. 1, 1974, pp. 70-78.

One promising aspect of enzyme-catalyzed polymer synthesis is the use of this technique to prepare materials having advantageous optical properties, such as chiral specificity. For example, W. Ladner et al. discuss enzyme-catalyzed reactions for producing esters of chiral epoxy alcohols in *Lipase-catalyzed Hydrolysis as a Route to Esters f Chiral Epoxy Alcohols*, Reprint from J.A.C.S., 1984, 106, 7250-7251. As another example, Kirchner et al. discuss the preparation of optically active alcohols on a small scale using transesterification reactions catalyzed by yeast lipase or pig liver carboxyl esterase in *J. Am. Chem. Soc.*, 1985, 107, 7072-7076.

Enzyme-catalyzed reactions involving diphenyl carbonate are of particular interest in relation to some of the areas discussed above, e.g., the production of phenol via hydrolysis. Furthermore, the enzyme-catalyzed transesterification of a diphenyl carbonate compound with an alcohol could provide a novel route for the preparation of useful products such as carbonate-containing polymers and optically active materials.

It is therefore an object of the present invention to provide a method for reacting diphenyl carbonate compounds to form a variety of useful materials.

It is a further object of the present invention to provide a method for obtaining optically active transesterification products from diphenyl carbonate compounds.

It is yet another object of the present invention to ovide a novel method for the preparation of polycarates.

SUMMARY OF THE INVENTION

The aforementioned objects are achieved by an improved method for performing an exchange reaction with a diphenyl carbonate compound, comprising reaction of the compound with a nucleophile such as water or an alcohol in the presence of an enzymatic catalyst having an active site capble of binding the diphenyl carbonate while retaining a catalytic residue after binding. In one embodiment, the exchange reaction is the enzyme catalyzed hydrolysis of diphenyl carbonate to produce phenol. In another embodiment, appropriate enzymes as discussed below can be used to catalyze the transesterification reaction of a diphenyl carbonate compound with a chiral material such as 2-butanol to form optically active products. In still another embodiment of this invention, diphenyl carbonate can be enzymatically catalyzed in a transesterification reaction with dihydric or polyhydric alcohols to form polycarbonate polymers, a well-known class of materials possessing characteristics suitable for a wide variety of products.

The term "enzyme" is being used herein interchangeably with "enzymatic catalyst".

DETAILED DESCRIPTION OF THE INVENTION

The diphenyl carbonate compounds of the present invention have the formula

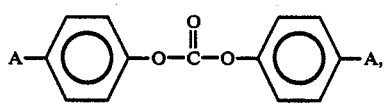

wherein each A is individually selected from the group consisting of hydrogen, lower alkyl groups, lower alkoxy groups, and halogens. "Lower" as used in reference to the alkyl and alkoxy groups is meant to describe four or less carbons in the main chain. Illustrative lower alkyl groups are methyl and isopropyl. Illustrative lower alkoxy groups are methoxy and ethoxy. Halogens suitable for A are bromine, fluorine, and chlorine. Unless otherwise indicated, the term "diphenyl carbonate" is meant to embrace all of the compounds described by formula I.

Any art-recognized method can be used to prepare such compounds, such as a Friedel-Crafts alkylation involving benzene or substituted benzene and phosgene in the presence of a Lewis acid catalyst such as aluminum chloride. The substituent A, when present as halogen, alkyl, or alkoxy, should only be in a position para to the carbonate linkage so that steric effects do not impede the enzyme-catalyzed exchange reaction.

The term "exchange reaction" as used herein is meant to describe hydrolysis when the diphenyl carbonate compound is reacted with water, and transesterification when reacted with other nucleophiles, such as various alcohols. Those of ordinary skill in the art appreciate that the fundamentals of enzymatic catalysis as used herein apply to both hydrolysis and transesterification.

The rate and completeness of the exchange reaction in the present invention is in part dependent on the particular enzymatic catalyst employed. Since enzymes are highly specific, those suitable for the present invention must have an active site capable of binding the diphenyl carbonate while retaining a catalytic residue after binding. The "active site" is the specific region of an enzyme which joins to the substrate, i.e., the diphenyl carbonate compound here, to form an enzyme-substrate (ES) complex. This concept is well-recognized in the art and described, for example, in *Biochemistry*, L. Stryer, Second Edition, W. H. Freeman and Company, 1981, the contents of which are incorporated herein by reference. As described in the Stryer reference, the substrate molecules may be bound to a cleft or crevice in the enzyme which contains several polar residues having special properties essential for binding and catalysis. Thus, suitable enzymes in this invention are those which must also retain a catalytic residue in the active site after binding. Additional discussion of these concepts may be found in the *Concise Encyclopedia of Biochemistry*, W. de Gruyter, Eng. Lang. Ed., 1983, incorporated herein by reference.

Enzymes fulfilling the requirements discussed above which are particularly suitable for the hydrolysis of diphenyl carbonate include Porcine liver esterase, *Candida Cylindracea* lipase (in crude form or, more preferably, in purified form), *Pseudomonas Fluorescens* cholesterol esterase, Rhizopus lipase, and Porcine cholesterol esterase. Other enzymes which are expected to be suitable for catalyzing the hydrolysis of diphenyl carbonate would include esterases which normally react with hydrophobic substrates. The enzymes mentioned above are well-known in the art and described, for example, in the *Enzyme Handbook*, T. Barman, Springer-Verlag Berlin-Heidelberg, 1969, incorporated herein by reference. One characteristic of enzymes suitable for the present invention is their particular turnover number, i.e., the number of molecules of a particular substrate which may be converted into a product per unit time per enzyme molecule when the enzyme is fully saturated with the substrate, as discussed in the Stryer text. Based on this characteristic, the most preferred enzymes for hydrolysis are the Porcine liver esterase and the *Candida Cylindracea* lipase (purified).

The hydrolysis may be carried out in a variety of water-miscible or water-immiscible organic solvents, with the proviso that the solvent solubilizes the diphenyl carbonate in water. Illustrative water-miscible organic solvents for the hydrolysis reaction include acetone, acetonitrile, methanol, ethanol, dioxane, and tetrahydrofuran. Illustrative water-immiscible solvents include hexane, methylene chloride, toluene, perfluorotributylamine, dimethyl carbonate, and various ethers, such as ethylether.

The choice of solvent sometimes affects the activity of a particular enzyme. For example, while *Chromobacterium Viscosum* lipase displays relatively high activity in a system containing 25% by weight acetone in water (and is within the scope of this invention), the same enzyme displays very low stability in a system consisting essentially of methylene chloride. Those skilled in the art are able to select the most appropriate solvent system for a particular enzyme without undue experimentation.

The amount of enzyme required depends in part on the catalytic activity of the particular enzyme. In general, about 0.05 millimole (mmole) to 10 mmole enzyme per mole of diphenyl carbonate compound is suitable for exchange reaction catalysis. The ratio of enzyme to substrate usually affects only the rate of reaction, and is not critical to process or yield. Those of ordinary skill in the art are able to determine the most effective catalyst level by observing the rate and character of hydrolysis in a particular system.

The particular techniques for performing hydrolysis are not critical to the present invention. In general, reaction mixtures may be maintained at a pH of about 4 to about 8 by the addition of a buffer solution, e.g., one containing a phosphate buffer and one or more alkali metal chlorides such as sodium chloride. Typically, the diphenyl carbonate is added to the reaction mixture as a stock solution in one of the solvents described above, while the particular enzyme may be advantageously supplied to the reaction mixture as a stock solution in the buffer solution. The particular order of adding the ingredients is not important, as long as thorough mixing is undertaken afterward. The production of phenol, the major hydrolysis product, may be monitored by a variety of methods well-known in the art, such as the use of chromatography or spectrophotometry. An example which follows further describes details of the hydrolysis reaction according to the present invention. In general, the ability of an enzyme to catalyze the hydrolysis of diphenyl carbonate is a reasonable predictor of the enzyme's ability to catalyze the transesterification of diphenyl carbonate.

As mentioned above, the enzyme-catalyzed exchange reaction of the present invention can be a transesterification reaction involving the diphenyl carbonate compound and an alcohol. While it is believed that any alcohol can participate in the transesterification reaction, those without very bulky organic groups attached thereto are preferred because their use results in higher transesterification rates. As further described below, dihydric or polyhydric alcohols are required when polymers are to be prepared according to the present invention. In general, the choice of a particular alcohol is dictated by the desired transesterification product.

Illustrative monohydric alcohols for the present invention have the formula ROH, wherein R is a lower alkyl group or a lower aromatic group. Examples of these alcohols are methanol, ethanol, isopropanol, n-propanol, 1-phenyl-2-methyl-2-propanol, 2-butanol, and p-cresol.

Monohydric alcohols of particular significance for the present invention are those characterized by a chiral molecular structure, i.e., at least one carbon center having four different substituents attached thereto. Examples of chiral alcohols are 2-butanol and 1-phenyl-2-methyl-2-propanol. Racemic mixtures of these materials display enantioselectivity, as further described in an example which follows. The selective production of one enantiomer of a particular compound by the presently disclosed invention can result in a very pure, optically active product useful for a variety of specialized applications.

As discussed above, dihydric or polyhydric alcohols are employed in the present invention when polymer products are desired. A variety of dihydric or polyhydric alcohols may be used in the present invention. Examples of suitable dihydric alcohols, i.e., diols, are ethylene glycol, propylene glycol, resorcinol, and pyrocatechol. A family of dihydric compounds suitable for the present invention are the di-(monohydroxylaryl)-alkanes, as described in U.S. Pat. No. 4,303,575, incorporated herein by reference. A particularly preferred compound of this type is 2,2-bis(4-hydroxyphenol)propane, commonly referred to as bisphenol A. The preparation of these materials is well-known in the art. As described in the examples which follow, the enzyme-catalyzed reaction of the diphenyl carbonate compound with a di-(monohydroxyaryl)-alkane such as bisphenol A results in a product mixture which includes bisphenol A polycarbonate material.

Another family of dihydric compounds suitable for the present invention are the spirobiindane bisphenols such as those described in commonly owned application Ser. No. 887,503, filed July 21, 1986 and incorporated herein by reference. Other examples of these compounds and their method of preparation are described in Baker et al., *J. Chem. Soc.*, 1421–1424 (1939), and in K. Stueben, *J. Poly. Sci.: Part A*, Volume 3, pp. 3209–3217 (1965), both incorporated herein by reference. As discussed above, the transesterification rate of diphenyl carbonate with a steric-hindered compound such as a spirobiindane bisphenol may be slower than with other compounds.

Examples of polyhydric alcohols suitable for reaction as described herein include glycerol, pyrogallol (1,2,3-trihydroxybenzene), phloroglucinol (1,3,5-trihydroxybenzene), and glucose.

As described above, enzymatic catalysts suitable for the present invention have an active site capable of binding the diphenyl carbonate while retaining a catalytic residue after binding. Illustrative enzymes suitable for the transesterification reaction are *Candida Cylindracea* lipase, Porcine liver esterase, *Pseudomonas fluorescens* cholesterol esterase, and *Rhizopus* lipase, all of which are well-known in the art and described in several of the references mentioned above. Other hydrolases (i.e., other esterases, amidases, and peptidases) with hydrophobic binding sites would also be suitable as enzymatic catalysts in certain embodiments of this invention. *Chromobacterium Viscosum* lipase is a suitable catalyst if the reaction takes place within a water-miscible system.

In preferred embodiments, the transesterification reaction is performed in a water-restricted environment, e.g., a hydrophobic organic solvent. The use of a water-restricted environment provides at least two advantages. First, it substantially reduces the hydrolysis of transesterification products in aqueous environments, thereby leading to higher product yield. Second, the enzymes are much more stable in a water-restricted environment than in an aqueous environment. However, a small amount of water should also be present, i.e., about 0.1% to about 0.4% by weight water, based on total weight of organic solvent and water. It is believed that this minimum amount of water provides a coating on hydrophilic surfaces of the enzyme and permits the enzyme to function effectively as a catalyst. The effects of particular organic solvents and of the level of water employed are further described in the examples which follow.

Illustrative hydrophobic organic solvents include methylene chloride, toluene, chloroform, carbon tetrachloride, dimethyl carbonate, octane, heptane, hexane, xylene, and fluorocarbon solvents such as FC-43, a product of 3M Company. Alkyl ethers, e.g., diethyl, dibutyl, and the like, are also suitable. Furthermore, other very hydrophobic solvents, i.e., those having a partition (distribution) coefficient logarithm greater than about 2, should also be suitable.

The enzyme-catalyzed transesterification reaction may be carried out by simply mixing the ingredients in any sequence. Typically, the water/organic solvent solution is first prepared, followed by the addition of the diphenyl carbonate compound and the alcohol. The enzyme is generally lyophilized and then added while the mixture is being thoroughly agitated.

In preferred embodiments involving the transesterification reaction, the enzymatic catalyst is first adsorbed onto an inert surface which is then inserted into the reaction medium containing the diphenyl carbonate compound and alcohol. Such a technique reduces the potential for the enzyme to agglomerate to itself and to the sides of the reaction vessel. Suitable inert materials include fumed silica, glass beads, polymer pellets, a glass slide, cellulose, filtration membranes, and other filtration aids such as Celite ® products. A commercial example of fumed silica is Cab-O-Sil ®, a product of the Cabot Corporation.

The particular technique of adsorbing the enzyme onto the inert material is not critical. One suitable method involves first dissolving the enzyme in a bicarbonate buffer solution and then adding the inert material under agitation. The examples which follow describe one suitable method for measuring adsorption and then isolating and storing the adsorbed material, which can be referred to as "the immobilized enzyme". Addition of this material to the reaction mixture is carried out under agitation, and the inert material may be removed from the mixture after completion of the reaction by art-recognized methods, e.g., centrifugation.

Another suitable technique known in the art involves the use of polymer matrix materials having chemically reactive groups attached thereon which will react with specific amino acids in proteins of the particular enzyme used. For example, a material such as cyanogen bromide activated sephrose can be used to covalently bind the enzyme, followed by addition of the bound complex to the reaction mixture. The remaining polymer is then removed from the mixture after the reaction is completed.

It is to be understood that the enzyme-catalyzed reaction of the diphenyl carbonate compound with an alcohol generally results in several different products, including various transesterification products and hydrolysis products. Reaction conditions may be varied as described herein in order to maximize the yield of a particular desired product. For example, the inclusion of only a minimum of water maximizes transesterification products which will not be appreciably hydrolyzed, as discussed above.

Although the present description relates particularly to water or alcohol being employed as the nucleophile reacting with diphenyl carbonate, other types of compounds might also serve as the nucleophile, such as amines, thiols, and oximes. These types of reactions may also be catalyzed by the enzymes discussed above. Furthermore, the resulting products may also display some useful properties, such as optical activity.

The following examples describe some embodiments of the present invention while also describing various methods for preparing exchange reaction products and for measuring product yields. However, the invention is not intended to be limited in any way by these examples. Percentages are by weight, unless otherwise indicated.

EXAMPLE 1

This example describes hydrolysis of diphenyl carbonate (unsubstituted) according to the present invention, employing a variety of enzymatic catalysts. A stock solution of diphenyl carbonate in acetone (10 mg/mL) was prepared beforehand. The enzymes used in Table 1 were also prepared beforehand as a stock solution at 1 mg/mL in the phosphate buffer composition described below. 500 uL of phosphate buffer solution (10 mM phosphate buffer, 150 mM NaCl, 5 mM KCl; pH=7.4), 200 uL acetone, 50 uL of the diphenyl carbonate stock solution, and 250 uL of the enzyme stock solution were combined in a reaction vessel and mixed thoroughly. The final reaction mixture content included 750 uL phosphate buffer, 250 uL acetone, 500 ug of diphenyl carbonate (2.33 umoles) and 250 ug of the enzyme (2.08 nmoles for the Candida lipase). Time points were taken by injecting 100 uL of the reaction mixture into a Waters Novapack C18 reversed-phase high pressure liquid chromatography column. Reactivity was monitored by phenol production at 254 nm. The enzymes which were employed have a half-life of approximately 10 hours in this reaction system. Table 1 describes the results:

TABLE 1
ENZYMATIC-CATALYZED HYDROLYSIS OF DIPHENOL CARBONATE (DPC)

| Sample No. | Enzyme | Hydrolysis Rate (TN/enz/min)* |
|---|---|---|
| 1 | Porcine Liver Esterase | 20,000 |
| 2 | *Candida Cylindracea* Lipase (purified) | 850 |
| 3 | *Chromobacterium Viscosum* Lipase | 290 |
| 4 | *Pseudomonas Fluoroscens* Cholesterol Esterase | 120 |
| 5 | Rhizupus Lipase | 110 |
| 6 | Porcine Cholesterol Esterase | 85 |
| 7 | *Candida Cyclindracea* Lipase (crude) | 25 |

*Moles of DPC reacting per mole enzyme per minute.

EXAMPLE 2

The enzyme-catalyzed transesterification of diphenyl carbonate in methylene chloride is described here. 12.5 uL of distilled water was added to 5 ml of a mixture of water-saturated methylene chloride and water-saturated hexane (0.25% by volume water). 45 mmoles of diphenyl carbonate and 45 mmoles of bisphenol A were added to the reaction mixture to form a final concentration of 10 mg/ml. 5 mg of *Candida Cylindracea* lipase (purified and immobilized) enzyme was also added to the mixture, followed by stirring at 250 rpm on a magnetic stirrer.

As determined by field desorption mass spectrometry analysis on the purified products, the product mixture contained the fractions listed in Table 2 after 25 minutes of reaction:

TABLE 2
TRANSESTERIFICATION PRODUCTS OF EXAMPLE 2

| Molecular Weight | Product(a) | Product Concentration (mM) Hexane | Methylene Chloride |
|---|---|---|---|
| 364 | ØOCOØOH | 26 | 290 |
| 482 | HOØOCOØOH | 10 | 12 |
| 500 | ØOCOØOCOØ | 8 | 4 |
| 873 | ØOCOØOCOØOCOØOH | 2 | 1 |
| 1000 | Products not Identified | Approx. 2 | 1 |

(a)

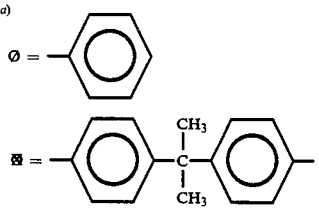

Ø = phenyl
☒ = bisphenol A group (—C₆H₄—C(CH₃)₂—C₆H₄—)

Due in part to the partial reversibility of the transesterification reaction under certain conditions, the product mixture changes over time. In this particular example, the products are relatively stable and are not hydrolyzed by the enzyme. Thus, longer reaction times result in higher molecular weight products. No detectable loss of enzymatic activity was observed after 3 days.

Table 3 describes the relative catalytic activity of the *Candida Cylindracea* lipase for diphenyl carbonate, as measured by high pressure liquid chromatography. The alcohol used was bisphenol A. The activities are provided as relative values based on a standard of one unit being equal to 0.15 turnovers per enzyme per minute for hydrolysis, and 6 turnovers per enzyme per minute for transesterification for an "unimmobilized enzyme" (1.5 turnovers/enz/min and 60 turnovers/enz/min, respectively, with the immobilized material).

TABLE 3
EFFECT OF ORGANIC SOLVENT AND WATER ON THE RELATIVE CATALYTIC ACTIVITY OF THE CANDIDA CYLINDRACEA LIPASE FOR DIPHENYL CARBONATE

| Solvent | MW g/mole | Hydrolysis Activity (c) dry | Water sat'd | +0.25% water | Transesterification Activity (+0.25% water) |
|---|---|---|---|---|---|
| DMC(a) | 90.08 | 0.00 | 2.6 | 2.8 | 0.0 |
| CH₂Cl₂ | 84.93 | 0.00 | 4.8 | 6.5 | 10.0 |
| CHCl₃ | 119.38 | 0.00 | 4.9 | 6.2 | 5.9 |
| Toluene | 92.15 | 0.01 | 1.2 | 1.5 | 0.0 |
| Diethyl ether | 74.12 | 0.00 | 13.5 | 13.1 | 1.0 |
| Hexane | 86.18 | 0.05 | 3.8 | 3.8 | 0.7 |
| FC-43(b) | 671.08 | 0.00 | 16.7 | 16.9 | 0.2 |

(a) Dimethyl carbonate
(b) Perfluorotrifluoroamine
(c) Saturation based on the equilibrium solubility for water in the solvent.

Table 2 demonstrates that hydrolysis competes with the transesterification reaction in water-saturated systems, while neither reaction can occur in the absence of water. The transesterification reaction is dominant at 0.25% by volume water, i.e., the water level described for the method of the present invention.

EXAMPLE 3

Figure 1:
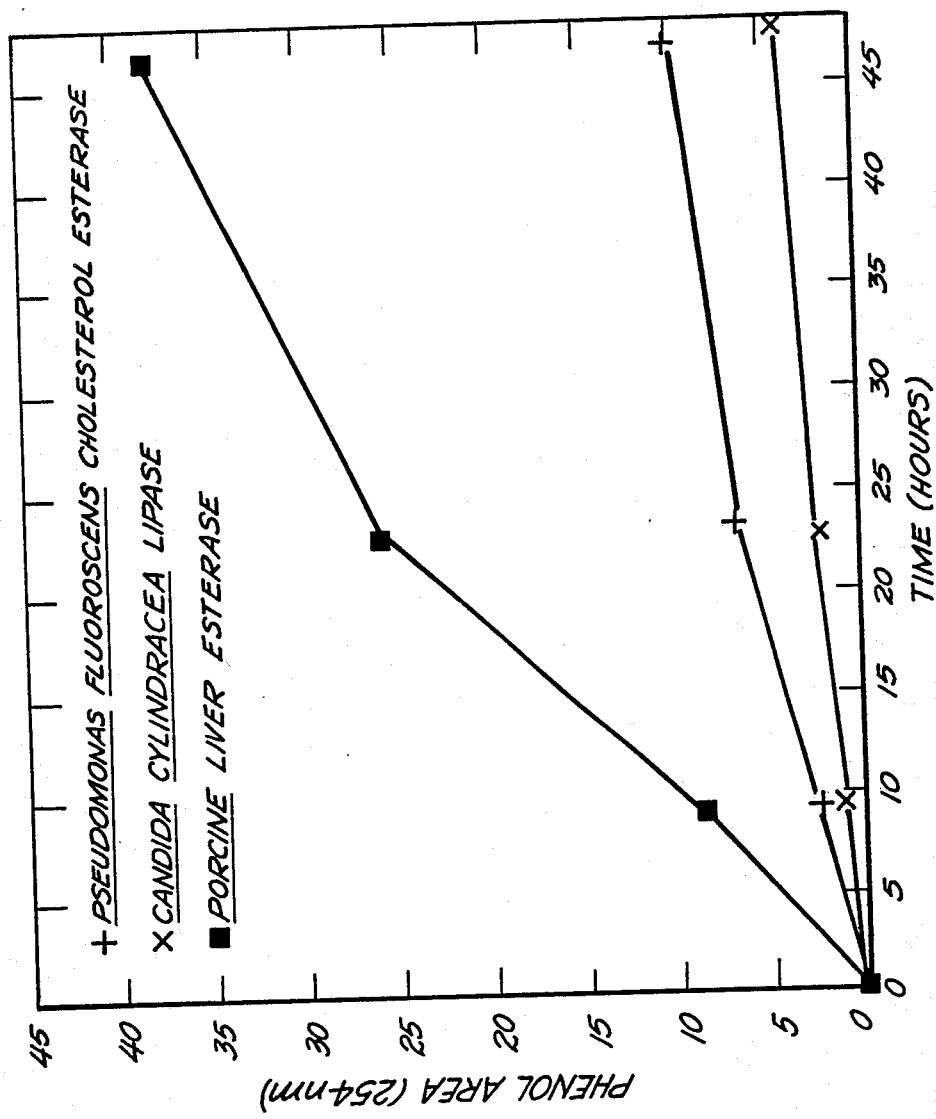
FIG. 1 depicts the catalytic activity of various enzymes used in the hydrolysis reaction described in Example 1. Hydrolytic activity was monitored by high pressure liquid chromatography (HPLC) with a peak area of the phenol product at 254 nm.
Figure 2:
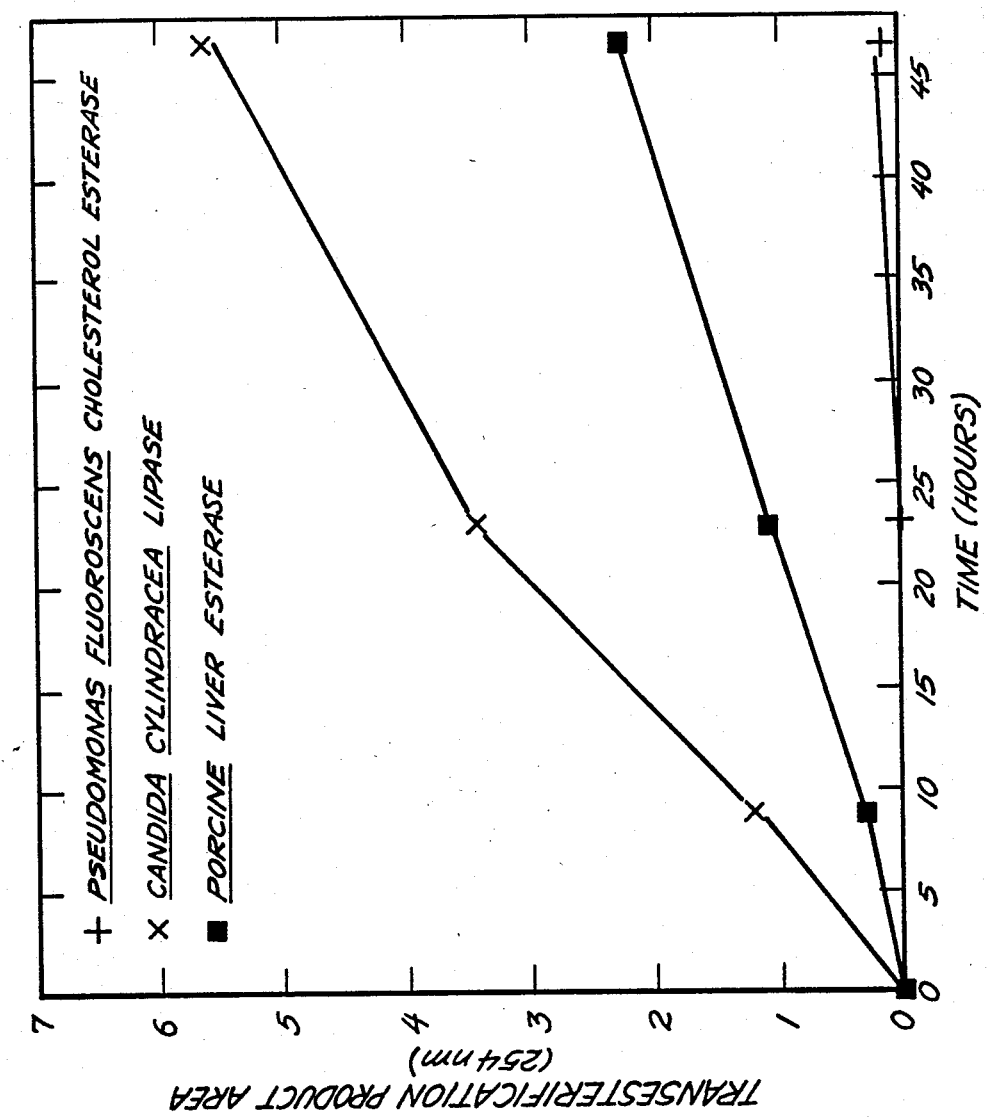
FIG. 2 represents the transesterification activity for those same enzymes as monitored by the HPLC peak area of the BPA-polycarbonate product at 254 nm.

Example 3 describes the reaction of diphenyl carbonate with a racemic mixture of 2-butanol. Tranesterification was performed in both water and organic solvent systems.

For the aqueous system, the reaction included 10% by volume 2-butanol (1 ml, 0.81 g, 11 mmoles), 9 ml of phosphate buffered saline, 5 mg *Candida Cylindracea* lipase (42 nmoles), and 1.5 g diphenyl carbonate (7 mmoles), bringing the total volume to 10 ml. The diphenyl carbonate was saturated at this concentration and precipitated to the bottom of the vessel. The final product was di(2-butanol) carbonate, which formed a second, lighter phase. Approximately half of the alcohol reacted before the reaction stopped, while some diphenyl carbonate precipitate remained at the bottom of the vessel.

In the organic system, an 8 ml reaction included 7.9 ml methylene chloride, 20 ul water (0.25% by volume), 100 mg diphenyl carbonate (0.47 mmoles), 100 ul 2-butanol (1.1 mmoles), and 10 mg lyophilized *Candida Cylindracea* lipase (84 nmoles). Aliquots were withdrawn every 30 minutes and assayed for enantiomeric purity of the 2-butanol.

Two methods were utilized to determine the enantiomeric excess of the remaining unreacted 2-butanol. Initially, optical rotation was measured with a polarimeter (maximum 13.9° for a 10 cm path length). For quantitation, the alcohol was derivatized with 1R(-) camphanic acid chloride, and the resulting diastereomers were resolved by HPLC according to the method of Mosher (Dale, J. A.; Dull, D. L.; and Mosher, H. S. (1969), *J. Org. Chem.*, 34, 2543–2549, incorporated herein by reference). Results indicated greater than 88% enantiomeric excess (ee), with an average value of 94% ee.

The production of enantiomerically-pure materials by this method can be of great benefit to the pharmaceutical industry, where there is often a need for biochemically active compounds having a particular stereochemical arrangement.

EXAMPLE 4

This example describes the use of an inert substrate to adsorb the enzyme prior to catalysis of the diphenyl carbonate-containing reaction mixture. In order to immobilize the particular enzyme employed, 1.0 g of fumed silica was combined with 50 ml. of 0.1 M bicarbonate buffer (pH=7) containing 10 mg/ml of enzyme. Adsorption to the silica surface was monitored by removing small aliquots at various times, clarifying the suspension by filtration or centrifugation, and measuring the amount of unadsorbed protein via UV absorption at 280 nm. The adsorption process was complete in less than 1 hour. The fumed silica was then spun down, and the supernatant fraction was decanted. The silica was resuspended in bicarbonate buffer without protein, and then again recovered by centrifugation to remove unadsorbed enzyme. The fumed silica pellet was then rapidly frozen in liquid nitrogen, lyophilized, and stored at −20° C.

The immobilized material had adsorbed 212 mg of enzyme per gram of final weight, based on UV absorption. Transesterification reactions were performed as in Example 2, with 30 mg of the immobilized material representing 6.4 mg of the enzyme calculated for use.

A tenfold increase in turnover number was demonstrated, as compared to the use of a non-immobilized enzyme under identical conditions.

Having described the invention with reference to specific materials and examples, those of ordinary skill in the art can readily select similar materials, process conditions, and procedures according to the guidelines described herein. Thus, the invention is to be limited only so far as is set forth in the claims which follow.

What is claimed is:

1. A method for performing an exchange reaction with a diphenyl carbonate compound of the formula

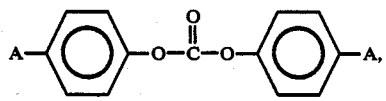

wherein each A is individually selected from the group consisting of hydrogen, lower alkyl groups, lower alkoxy groups, and halogens, comprising the reaction of the diphenyl carbonate compound with water or an alcohol in the presence of an enzymatic catalyst having an active site capable of binding the diphenyl carbonate while retaining a catalytic residue after binding.

2. The method of claim 1 wherein the exchange reaction is transesterification, and the enzymatic catalyst is selected from the group consisting of *Candida Cylindracea* lipase, Porcine liver esterase, *Pseudomonas Fluorescens* cholesterol esterase, and Rhizopus lipase.

3. The method of claim 1 wherein the exchange reaction is transesterification and the enzymatic catalyst is *Candida Cylindracea* lipase.

4. The method of claim 2 wherein the alcohol has the formula ROH, R being a lower alkyl group or a lower aromatic group.

5. The method of claim 4 wherein the alcohol is in the form of a racemic mixture, and wherein at least one of the products of the transesterification reaction is optically active.

6. The method of claim 5 wherein the alcohol is 2-butanol.

7. The method of claim 2 wherein the alcohol is dihydric or polyhydric.

8. The method of claim 7 wherein the alcohol is a spirobiindane bisphenol.

9. The method of claim 7 wherein the alcohol is a di-(monohydroxylaryl)-alkane.

10. The method of claim 9 wherein the di-(monohydroxylaryl)-alkane is bisphenol A.

11. The method of claim 7 wherein the reaction is performed in a water-restricted environment which maximizes transesterification products and minimizes hydrolysis by-products.

12. The method of claim 11 wherein the water-restricted environment comprises a hydrophobic solvent and between about 0.1% and 0.4% by weight water.

13. The method of claim 12 wherein the solvent is methylene chloride.

14. The method of claim 12 wherein the enzymatic catalyst is first adsorbed onto an inert surface which is then inserted into the reaction medium containing the diphenyl carbonate compound and the water or alcohol.

15. The method of claim 14 wherein the inert surface is that of fumed silica.

16. The method of claim 1 wherein the exchange reaction is hydrolysis.

17. A method for the preparation of polycarbonates, comprising the transesterification of a diphenyl carbonate compound with a dihydric phenol in the presence of an enzymatic catalyst selected from the group consisting of *Candida Cylindracea* lipase, Porcine liver esterase, Rhizopus lipase, and *Pseudomonas Fluorescens* cholesterol esterase.

18. The method of claim 17 wherein the dihydric phenol is bisphenol A.

19. The method of claim 18 wherein transesterification occurs in a water-restricted environment.

* * * * *